(12) United States Patent
Gunnarshaug

(10) Patent No.: US 7,117,543 B1
(45) Date of Patent: Oct. 10, 2006

(54) NOSE PROTECTION SHIELD

(76) Inventor: Angel Gunnarshaug, 2625 Grand Oaks Dr., Westlake Village, CA (US) 91361

( * ) Notice: Subject to any disclaimer, the term of this patent is extended or adjusted under 35 U.S.C. 154(b) by 240 days.

(21) Appl. No.: 10/686,392

(22) Filed: Oct. 14, 2003

(51) Int. Cl.
 *A42B 1/18* (2006.01)
(52) U.S. Cl. .................. 2/206; 2/9; 128/857; 128/858; 602/6; 351/155
(58) Field of Classification Search .................. 2/206, 2/9; 128/858, 857; 351/155; 602/6
 See application file for complete search history.

(56) References Cited

U.S. PATENT DOCUMENTS

| | | | |
|---|---|---|---|
| 1,436,313 A | 11/1922 | Hafer | |
| 1,761,664 A | 6/1930 | Harris | |
| 2,233,698 A | 3/1941 | Girovard | |
| 2,519,561 A | 8/1950 | Gillman et al. | |
| 3,594,813 A | 7/1971 | Sanderson | |
| 3,742,943 A | 7/1973 | Malmin | |
| 3,835,848 A | 9/1974 | Berner | |
| 3,955,885 A * | 5/1976 | Aronsohn | 351/155 |
| 4,213,452 A | 7/1980 | Shippert | |
| 4,274,402 A | 6/1981 | Shippert | |
| D274,437 S | 6/1984 | Dianitsch | |
| 4,534,342 A | 8/1985 | Pexa | |
| 4,635,625 A | 1/1987 | Teeple | |
| 4,674,133 A | 6/1987 | Oschner | |
| 4,773,408 A | 9/1988 | Cilento et al. | |
| 4,786,159 A | 11/1988 | Piazza, Sr. et al. | |
| 4,941,212 A * | 7/1990 | Liff | 2/206 |
| D323,410 S | 1/1992 | Jacobson | |
| 5,438,710 A | 8/1995 | McDonald et al. | |
| 5,592,687 A | 1/1997 | Lajeunesse | |
| 5,682,607 A * | 11/1997 | Klein | 2/9 |
| 5,976,173 A | 11/1999 | Berke | |
| D427,370 S | 6/2000 | Kalafsky et al. | |
| 6,206,902 B1 * | 3/2001 | Morikane | 606/204.15 |
| 6,299,605 B1 * | 10/2001 | Ishida | 604/289 |
| 6,419,687 B1 | 7/2002 | Berke | |
| 6,649,181 B1 * | 11/2003 | Miner | 424/402 |

* cited by examiner

Primary Examiner—John J. Calvert
Assistant Examiner—Alissa J. Tompkins
(74) Attorney, Agent, or Firm—Jack C. Munro

(57) ABSTRACT

A nose protection shield designed to be custom fitted to the exterior shape of a nose which is constructed of a hydrophilic thermoplastic having a thickness of between one-half millimeter to one millimeter. The nose protection shield is constructed by making a cast of the person's nose by applying a first hardenable material onto the nose, causing this first hardenable material to harden, removing the cast after such is hardened, filling of the cavity of the cast with a second hardenable material, permitting the second hardenable material to harden to form a model, removing the model from the cast, placing a thin, flexible plastic sheet on the model, drawing a vacuum in proximity of the model which causes the sheet to be drawn tightly against the model, apply heat for a short period of time to the sheet to a sufficient level to cause the at-rest shape of the sheet to be deformed and assume the new configuration of the model, and then removing of the sheet from the model.

1 Claim, 3 Drawing Sheets

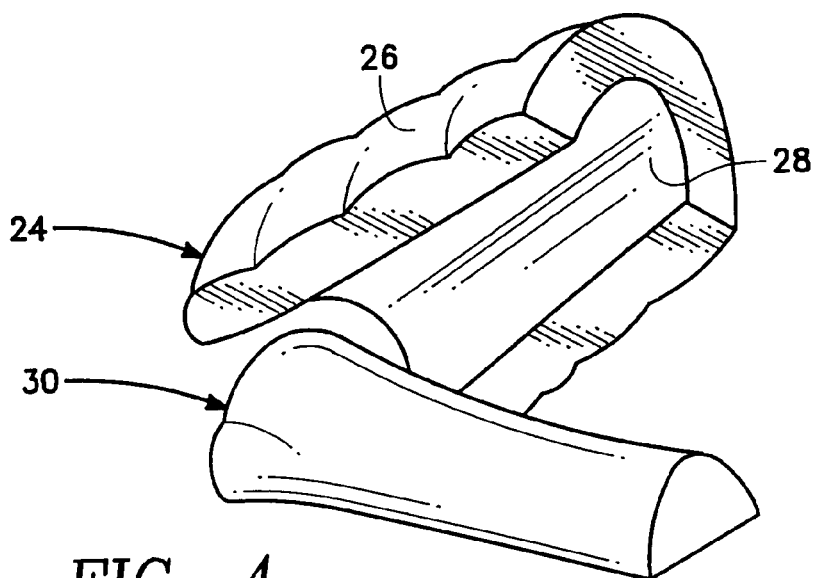
FIG. 4
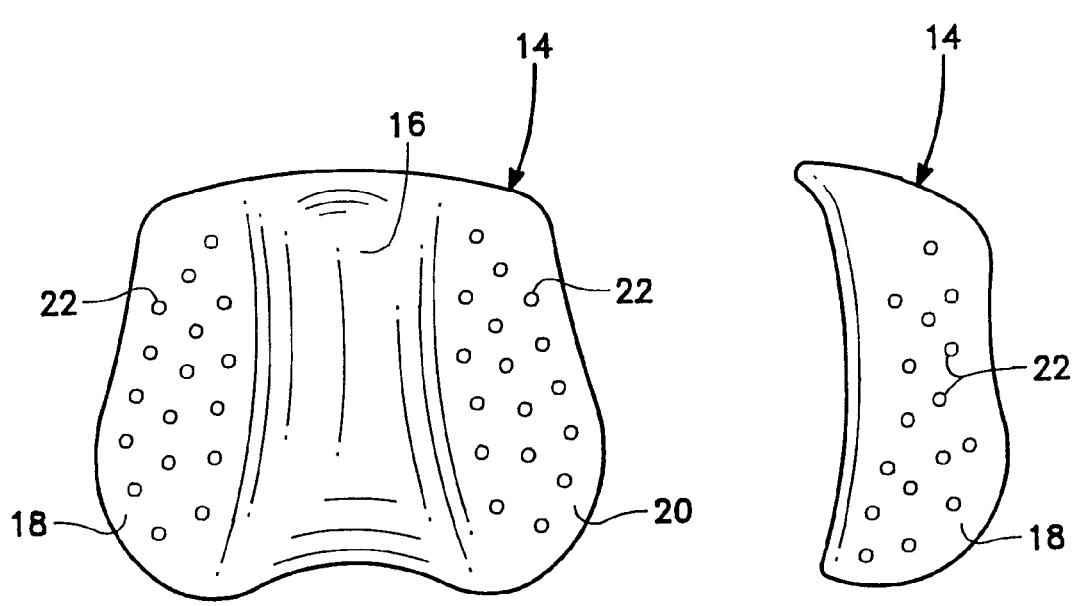
FIG. 5
FIG. 6
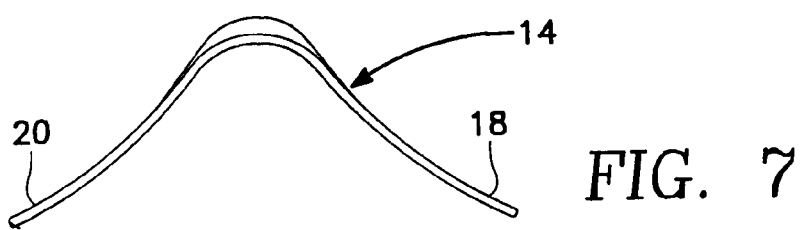
FIG. 7

NOSE PROTECTION SHIELD

BACKGROUND OF THE INVENTION

1. Field of the Invention

The field of this invention relates to nose protection shields and more particularly to a nose protection shield which can be utilized to eliminate eyeglass indentations within the nose after the individual has had a rhinoplasty.

2. Description of the Related Art

Rhinoplasty is a common surgical technique of plastic surgeons. After a rhinoplasty is performed, the nose will assume an enlarged shape due to swelling. It normally takes the nose several months to totally recover from a rhinoplasty. The skin of the nose after a rhinoplasty is exceedingly sensitive and very vulnerable to deformation and impression.

In the past, wearers of eyeglasses have found it exceedingly difficult to wear eyeglasses after having a rhinoplasty. This makes for a very difficult situation as times it is mandatory for these individuals to wear eyeglasses, such as for driving of an automobile, truck or motorcycle. There is a need to fabricate and construct a device that would permit wearers of eyeglasses to wear eyeglasses for the period of time after a rhinoplasty until the nose completely heals.

Previously, there have been attempts at designing shields for a nose. However, in the past, these shields have been designed to protect the nose against natural elements, such as sun, wind and rain. To the inventor's knowledge, it has not been known to construct a nose protection shield that is designed explicitly for usage after an individual has had a rhinoplasty.

SUMMARY OF THE INVENTION

After a plastic surgeon performs rhinoplasty on a patient, the surgeon places a cast over the nose to keep its new form and shape. This is the same type of cast a doctor would place on a broken leg or arm. Approximately one week later the surgeon removes the cast which is now formed to the new shape of the nose. The doctor or patient then mails the cast to the person utilizing the present invention which is then used to produce a thin, hydrophilic, thermoplastic shield which is then custom designed for the patient. The shield is formed by pouring a hardening stone material against the inside surface of the cast creating a model after hardening. The shield is then made from this model.

A first basic embodiment comprises a method of making a nose protection shield which comprises the steps of making a cast of a person's nose by applying a first hardenable material on the exterior surface of the nose, causing this first hardenable material to harden forming the cast, removing of the cast after such is hardened where the cast has a cavity the precise shape of the nose, filling of the cavity with a second hardenable material, permitting the second hardenable material to harden forming a model, removing the model from the cast, placing a thin, flexible, sheet material on the model, inserting the model and the sheet within a forming machine, drawing a vacuum which presses the sheet tightly against the model, applying heat for a short period of time to the sheet which changes the at-rest configuration from the sheet to the shape of the nose, removing the sheet and the model from the forming machine, removing the sheet from the model and then trimming of the sheet and forming ventilation holes in the now formed shield.

A further embodiment of the present invention is where the just previous embodiment is modified by the sheet being constructed of a hydrophilic material that self adheres to the nose.

A further embodiment of the present invention is where the just previous embodiment is modified by the sheet being constructed of a thermal plastic material having a thickness between one-half millimeter to one millimeter thick.

A second basic embodiment of the present invention is directed to a nose protection shield constructed of a thin, hydrophilic, thermoplastic material which is custom designed to fit to the exterior surface of one's nose.

A further embodiment of the present invention is where the just previous embodiment is modified by the shield having a thickness between one-half millimeter to one millimeter.

BRIEF DESCRIPTION OF THE DRAWINGS

For a better understanding of the present invention, reference is to be made to the accompanying drawings. It is to be understood that the present invention is not limited to the precise arrangement shown in the drawings.

FIG. 4 is an isometric view showing the relationship between the cast and the model which is formed from the cast which is then used to produce the nose protection shield of the present invention;

FIG. 5 is a back side view of the nose protection shield of the present invention;

FIG. 6 is a side elevational view of the nose protection shield of the present invention;

FIG. 7 is a top plan view of the nose protection shield of the present invention.

DETAILED DESCRIPTION OF THE INVENTION

Figure 1:
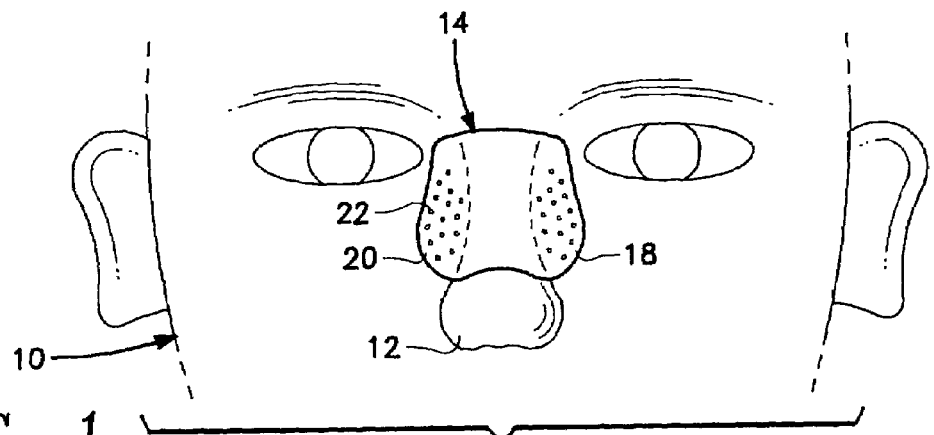
FIG. 1 is a front view showing a user's face on which has been applied the nose protection shield of the present invention to the nose of the person's face.
Figure 2:
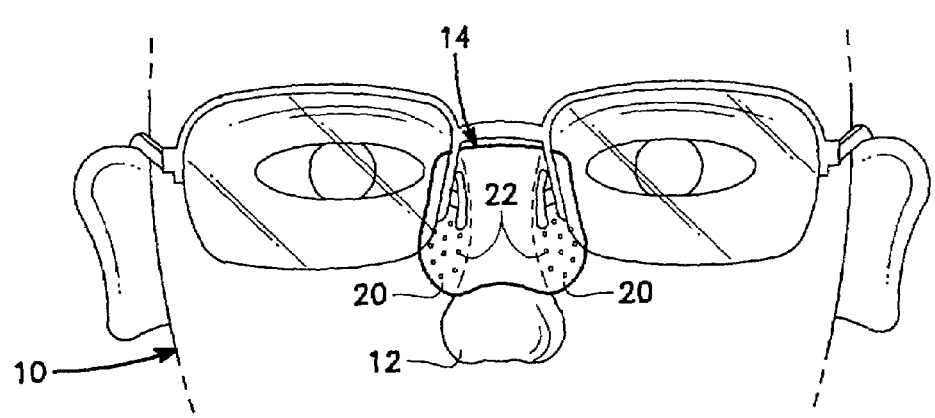
FIG. 2 is a view similar to FIG. 1 but showing the user wearing eyeglasses in conjunction with the nose protection shield.

Referring particularly to FIG. 1, there is shown a face 10 of a user which has a nose 12. Mounted on the nose 12 is the nose protection shield 14 of this invention. The shield 14 is to be constructed of a hydrophilic, thermoplastic material with generally a copolyester being a common type of material. The shield in thickness will generally range between one-half millimeter to one millimeter. The shield 14 is flexible. It has been found that if the shield is hydrophilic that its propensity to absorb moisture tends to establish a self-adherence to the surface of the nose 12. In other words, the shield 14 is to conform precisely to the shape of the nose 12 and when placed on the nose 12 will remain in that position without the use of any fasteners of any type.

The shield 14 has a centrally located longitudinal cavity 16 which is located between side flanges 18 and 20. The longitudinal cavity 16 is to have located therein the outwardly protruding configuration of the nose 12 with the side flanges 18 and 20 resting against the sides of the nose 12 and then extending downward to rest on the cheek area of the face 10. Each of the side flanges 18 and 20 include a series of ventilation holes 22. The purpose of the ventilation holes 22 is to provide air to pass through to permit any perspiration to evaporate to provide comfortable use of the shield 14.

Figure 3:
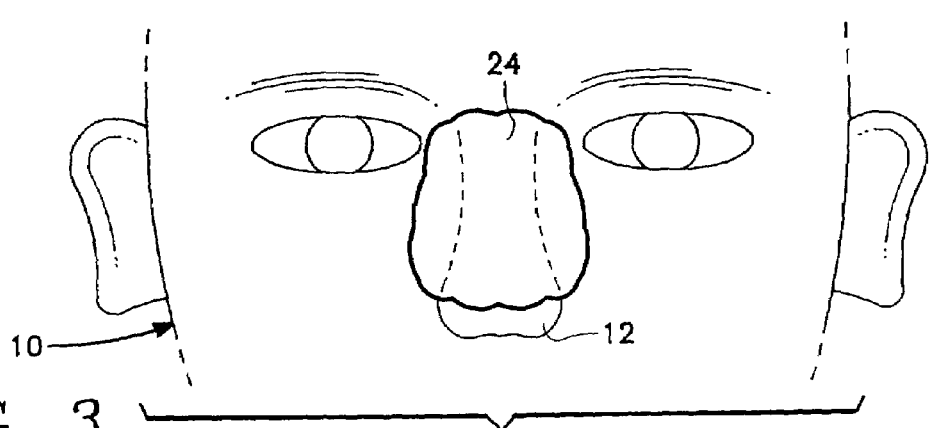
FIG. 3 is a view similar to FIG. 1 but showing the application of the first hardenable material on the nose to produce the cast from which the nose protection shield is to be ultimately produced.

It is to be reiterated that the shield 14 is custom designed for the particular user. In order to achieve this custom designing, a quantity of a paste, gel or other similar type of material is applied to the user's nose with this quantity being represented as glob 24 in FIG. 3. The glob 24 could comprise a plaster, such as plaster of Paris. The glob 24 is applied in a paste configuration, and after a short period of time will harden forming a cast 26. The cast 26, when removed from the nose 12, has an internal cavity 28.

The internal cavity 28 is to be filled with a second hardenable material which could comprise a rubber, gel, plaster or any other desirable material. Prior to inserting of the second hardenable material in the cavity 28, the surface of the cavity 28 may be coated with a release agent, which generally would be some form of an oil, which is not shown. Such release agents are exceedingly common usage in conjunction with molding. After the second hardenable material hardens and is extracted from the cavity 28, there is formed a model 30.

The model 30 is to be inserted on a perforated platform 32 of a forming machine 34. The holes 36 of the perforated platform 32 are connectable to a vacuum source which can be activated by pressing of switch 38 which is mounted on machine base 40. Mounted also on machine base 40 is a vertically extending rail 42. Mounted on the rail 42 is a frame 44. The frame 44 includes a center opening 46. Mounted in a taut manner across the center opening 46 is a sheet 48. The sheet 48 is of hydrophilic material that eventually will become the shield 14. It is to be noted that the sheet 48 is actually transparent. However, it is not necessary within the scope of this invention that the sheet 48 be transparent. Also mounted on the rail 42 and located above the frame 44 is a cover 50. Mounted within the cover 50 is a heating coil 52.

Figure 8:
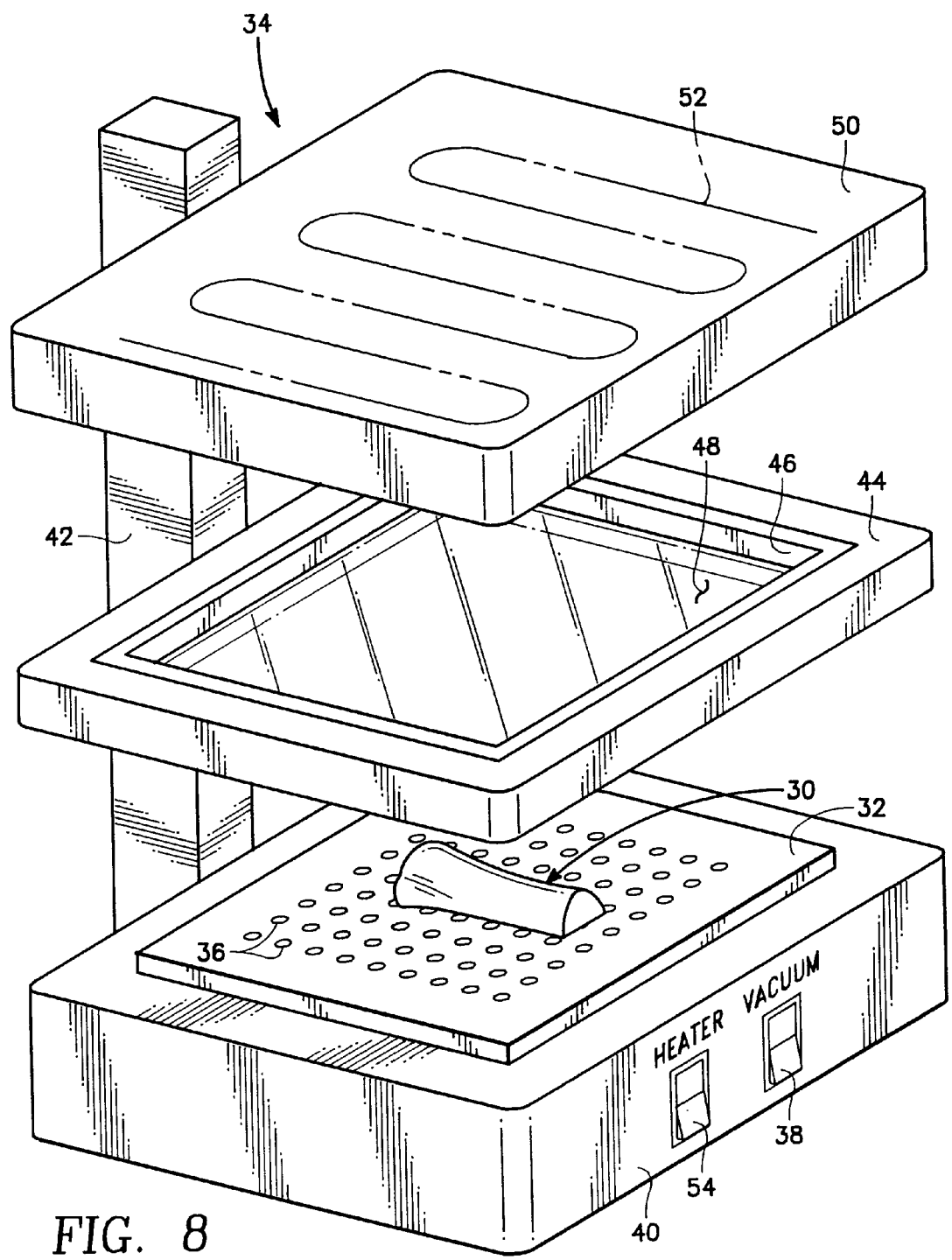
FIG. 8 is an isometric view showing a forming machine which is utilized to produce the nose protection shield of the present invention.

The operation of the forming machine 34 of this invention is as follows: The model 30 is positioned generally centrally on the perforated plate 32. The vacuum switch 38 is then pressed generating a vacuum and the frame 44 is then slid on the rail 42 until the sheet 48 surrounds the upper surface of the model 30 with the frame 44 coming into contact with the base 40. In essence, an enclosed chamber is achieved which sucks the sheet 48 into tight adherence about the surface of the model 30. The cover 50 is then slid on the rail 42 to where it abuts against the upper surface of the frame 44. The switch 54 is then pressed which turns on the heater by causing electricity to be supplied to the coils 52 producing heat. This heat is transmitted directly to the sheet 48, and in a manner of a few seconds thermoplastically changes the at-rest shape of the sheet 48 from the flat planar configuration shown in FIG. 8 to assume the shape of the exterior surface of the model 30. The switch 54 is then pressed which deactivates the heater and the cover 50 moved again to the position shown in FIG. 8. The sheet 48 is then removed from the forming machine 34 with the frame 44 then moved again to the position shown in FIG. 8. The vacuum switch 38 is then moved to the deactivated position. Sheet 48 is then removed from the model 30. The sheet 48 is then trimmed resulting in the production of the shield 14 in the shape shown in FIGS. 5–7. The ventilation holes 22 are then formed within the shield 14 by using of an appropriate penetrating tool.

What is claimed is:

1. A method of making a nose protection shield comprising the steps of:

making a direct cast of a human nose by applying a first hardenable material on the nose;

causing said first hardening material to harden forming said cast;

removing of said cast after such is hardened where the cast has a cavity the precise shape of the exterior surface of the nose;

filling of said cavity with a second hardenable material;

permitting said second hardenable material to harden forming a model;

removing said model from said cast;

placing a thin, flexible, hydrophilic plastic sheet on said model;

inserting said model and said sheet within a forming machine;

drawing a vacuum which presses said sheet tightly against said model;

applying heat for a short period of time to said sheet with the heat being sufficient to change the at-rest configuration of said sheet to the configuration of said model;

removing said sheet and said model from said forming machine;

removing said sheet from said model;

trimming said sheet to a desired size;

forming ventilation holes in said sheet which results in said nose protection shield; and whereby said nose protection shield can now be worn by an individual for which said nose protection shield was custom designed permitting the individual to wear eyeglasses which have a bridge which will rest on said noise protection shield and not form an indentation within the skin of the nose and because said shield is hydrophilic it absorbs moisture from the skin of the nose causing self-adherence to the nose preventing unauthorized removal of said shield.

* * * * *